United States Patent
Uber, III et al.

(10) Patent No.: US 9,623,191 B2
(45) Date of Patent: Apr. 18, 2017

(54) INFORMATION SENSING SYRINGE

(71) Applicant: MEDRAD, INC., Indianola, PA (US)

(72) Inventors: Arthur E. Uber, III, Pittsburgh, PA (US); Charles Marsh, Cranberry Township, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 612 days.

(21) Appl. No.: 13/783,226

(22) Filed: Mar. 1, 2013

(65) Prior Publication Data
US 2014/0249410 A1 Sep. 4, 2014

(51) Int. Cl.
| | |
|---|---|
| A61B 6/00 | (2006.01) |
| A61M 5/315 | (2006.01) |
| A61M 5/00 | (2006.01) |
| A61M 5/168 | (2006.01) |
| A61M 5/145 | (2006.01) |
| A61M 5/20 | (2006.01) |

(52) U.S. Cl.
CPC ........ *A61M 5/31573* (2013.01); *A61M 5/007* (2013.01); *A61M 5/1452* (2013.01); *A61M 5/16831* (2013.01); *A61M 5/16877* (2013.01); *A61M 5/20* (2013.01); *A61M 5/31513* (2013.01); *A61M 2205/33* (2013.01)

(58) Field of Classification Search
None
See application file for complete search history.

(56) References Cited

U.S. PATENT DOCUMENTS

| | | | |
|---|---|---|---|
| 4,401,108 A | * | 8/1983 | Galkin et al. ............... 600/5 |
| 5,806,519 A | | 9/1998 | Evans, III et al. |
| 5,808,203 A | | 9/1998 | Nolan, Jr. et al. |
| | | (Continued) | |

FOREIGN PATENT DOCUMENTS

| | | |
|---|---|---|
| EP | 2000161 A1 | 12/2008 |
| WO | 93/10834 | 6/1993 |
| WO | 2014067879 A1 | 5/2014 |

OTHER PUBLICATIONS

The International Search Report and Written Opinion mailed Aug. 5, 2014 of corresponding PCT Application No. PCT/US2014/019229.

(Continued)

*Primary Examiner* — James Kish
(74) *Attorney, Agent, or Firm* — Joseph L. Kent; David Schramm; James R. Stevenson

(57) ABSTRACT

Syringe systems and flow control systems configured to detect information associated with a liquid material are described. The syringe systems may include a syringe body for housing the liquid material and an injector piston for expelling the liquid material out of the syringe through a discharge outlet at a distal end of the syringe body. Components of the syringe, such as an injector piston, may include sensors configured to measure and/or detect a property of the liquid material, such as concentration, pH, or radioactivity. The flow control system may include a pinch valve and a platen arranged about a fluid delivery channel. Flow within the fluid delivery channel may be controlled by increasing (squeezing the fluid delivery channel) or decreasing the distance between the pinch valve and the platen. Components of the flow control system may include detectors configured to detect properties of fluid in the fluid control channel.

14 Claims, 8 Drawing Sheets

(56) References Cited

U.S. PATENT DOCUMENTS

| | | | |
|---|---|---|---|
| 6,179,569 B1 | 1/2001 | Kojima et al. | |
| 6,317,623 B1 | 11/2001 | Griffiths et al. | |
| 6,743,202 B2 | 6/2004 | Hirschman et al. | |
| 7,553,294 B2 | 6/2009 | Lazzaro et al. | |
| 2001/0034506 A1* | 10/2001 | Hirschman et al. | 604/207 |
| 2005/0277833 A1 | 12/2005 | Williams, Jr. | |
| 2008/0183122 A1* | 7/2008 | Fisher | A61M 5/31511 604/21 |
| 2008/0308580 A1* | 12/2008 | Gaydos et al. | 222/333 |
| 2011/0178359 A1 | 7/2011 | Hirschman et al. | |
| 2011/0264033 A1* | 10/2011 | Jensen et al. | 604/65 |
| 2012/0226447 A1 | 9/2012 | Nelson et al. | |

OTHER PUBLICATIONS

The International Preliminary Report of Patentability and Written Opinion mailed Sep. 1, 2015 from corresponding PCT Application No. PCT/US2014/019229.

* cited by examiner

INFORMATION SENSING SYRINGE

BACKGROUND

Syringes are used to deliver various types of liquid medications and contrast agents, such as pharmaceuticals, saline solution, and radioactive imaging agents. A typical syringe includes a syringe body configured to house a liquid and an injector piston arranged within the syringe body. The injector piston provides an expulsion force as it progresses through the syringe body, causing the liquid to be expelled through a discharge outlet at a distal end of the syringe body. In many cases, one or more properties of the liquid medication or contrast agent, including concentration or radioactivity, must be within certain ranges before delivery to a patient. For example, the properties may be used to indicate an effectiveness or to determine proper dosing of the liquid medication or contrast agent.

However, measurement of such properties is not possible once the liquid is in the syringe body of a syringe. In addition, although measurements may be obtained before the liquid is placed in the syringe, certain properties may change between the time of measurement and when the liquid is actually injected into the patient. As such, health care providers and patients may not know for certain whether properties associated with a liquid medication or contrast media are within acceptable limits.

SUMMARY OF THE INVENTION

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

In an embodiment, a syringe system may comprise a syringe body comprising a proximal open end and at least one distal discharge outlet. The syringe body may be configured to house a liquid substance. A plunger may be positioned in the syringe body forming a seal with an inner wall of the syringe body. An injector piston may be configured to be received by the proximal open end and to slide within the syringe body. In addition, the injector piston may be configured to engage the plunger as it slides within the syringe body to expel, draw in, or move the liquid substance through the at least one discharge outlet. At least one sensor may be provided that is configured to measure at least one property of the liquid substance.

In an embodiment, a device for automatically injecting a radioactive liquid substance may comprise a syringe and an injection piston. The syringe may comprise a syringe body comprising a proximal open end and at least one distal discharge outlet, the syringe body being configured to house a liquid substance and a plunger arranged within the syringe body forming a seal with an inside surface of the syringe body. The injector piston may be configured to be received by the proximal open end and to slide within the syringe body. In addition, the injector piston may be configured to engage the plunger as it slides within the syringe body to expel, draw in, or move the radioactive liquid substance through the at least one discharge outlet. At least one sensor may be provided that is configured to measure at least one radioactive property of the radioactive liquid substance. A syringe shield may be provided that covers at least a portion of the syringe body.

In an embodiment, an automated injector system for injecting a liquid material may comprise a syringe and an injection piston. The syringe may comprise a syringe body comprising a proximal open end and at least one distal discharge outlet, the syringe body being configured to house a liquid substance and a plunger arranged within the syringe body forming a seal with an inside surface of the syringe body. The injector piston may be configured to be received by the proximal open end and to slide within the syringe body. In addition, the injector piston may be configured to engage the plunger as it slides within the syringe body to expel, draw in, or move the radioactive liquid substance through the at least one discharge outlet. At least one sensor may be provided that is configured to generate liquid material data by measuring at least one property of the liquid substance. The automated injector system may comprise a computing device comprising at least one processor and at least one non-transitory computer-readable storage medium operatively coupled to the at least one processor. The at least one non-transitory computer-readable storage medium comprising one or more programming instructions that, when executed, cause the at least one processor to: receive the liquid material data and generate at least one injection event based on the liquid material data. In another embodiment, the at least one non-transitory computer-readable storage medium of the automated injector system may further comprise one or more programming instructions that, when executed, cause the at least one processor to store at least a portion of the liquid material data in a health information system. In a further embodiment, the at least one sensor may comprise a plurality of sensors configured to measure a first property of the liquid substance and the at least one non-transitory computer-readable storage medium of the automated injector system may further comprise one or more programming instructions that, when executed, cause the at least one processor to compare measurements of the first property at each of the plurality of sensors to redundantly check an accuracy of the measurements.

In an embodiment, a system for automatically filling a syringe with a radioactive liquid substance may comprise a radioactive liquid substance source configured to store the radioactive liquid substance; and a syringe filling element configured to obtain the radioactive liquid substance from the radioactive liquid substance and to fill a syringe therewith. The syringe may comprise a syringe body comprising a proximal open end and at least one distal discharge outlet, the syringe body being configured to house a liquid substance, and a plunger arranged within the syringe body forming a seal with an inside surface of the syringe body, an injector piston configured to be received by the proximal open end and to slide within the syringe body, the injector piston being configured to engage the plunger as it slides within the syringe body to expel, draw in, or move the radioactive liquid substance through the at least one discharge outlet, at least one sensor configured to measure at least one radioactive property of the radioactive liquid substance, and a syringe shield covering at least a portion of the syringe body.

In an embodiment, a fluid delivery channel flow control system may comprise a force concentration point and a platen arranged to opposedly contact a fluid delivery channel positioned therebetween. A force assembly may be configured to move one of the force concentration point and the platen in a first direction to reduce a distance therebetween, thereby generating a pressing force on the fluid delivery channel and reducing a flow of a fluid within the fluid delivery channel, and in a second direction to increase the distance, thereby reducing at least a portion of the pressing force on the fluid delivery channel and increasing the flow of the fluid in the fluid delivery channel.

BRIEF DESCRIPTION OF THE DRAWINGS

In the following detailed description, reference is made to the accompanying drawings, which form a part hereof. In the drawings, similar symbols typically identify similar components unless context dictates otherwise. The illustrative embodiments described in the detailed description, drawings, and claims are not meant to be limiting. Other embodiments may be utilized and other changes may be made, without departing from the spirit or scope of the subject matter presented herein. It will be readily understood that the aspects of the present disclosure, as generally described herein and illustrated in the Figures, can be arranged, substituted, combined, separated, and designed in a wide variety of different configurations, all of which are explicitly contemplated herein.

DETAILED DESCRIPTION

The terminology used in the description is for the purpose of describing the particular versions or embodiments only, and is not intended to limit the scope.

The word "proximal" refers to a direction relatively closer to a clinician or automated system (e.g., automatic syringe injector) using the device described herein, and the word "distal" refers to a direction relatively further from the clinician or automated system. For example, the end of a syringe (e.g. syringe needle) placed within the body of a patient or syringe tubing is considered a distal end of the syringe, while the plunger end of the syringe is a proximal end of the syringe.

The present disclosure is directed to syringes configured to sense information associated with a liquid disposed within the syringe. In an embodiment, a syringe plunger and/or injector piston of the syringe may comprise one or more sensors arranged to measure one or more properties of a liquid disposed within the syringe. In another embodiment, the syringe plunger and/or injector piston of the syringe may have a cavity disposed therein to receive a portion of the liquid. In this embodiment, one or more sensors may be arranged within the cavity and may contact the liquid to measure one or more properties thereof. The sensors may be in communication with one or more logic devices, such as a computing device or electronic medical device, configured to receive the measured information.

Figure 1A:
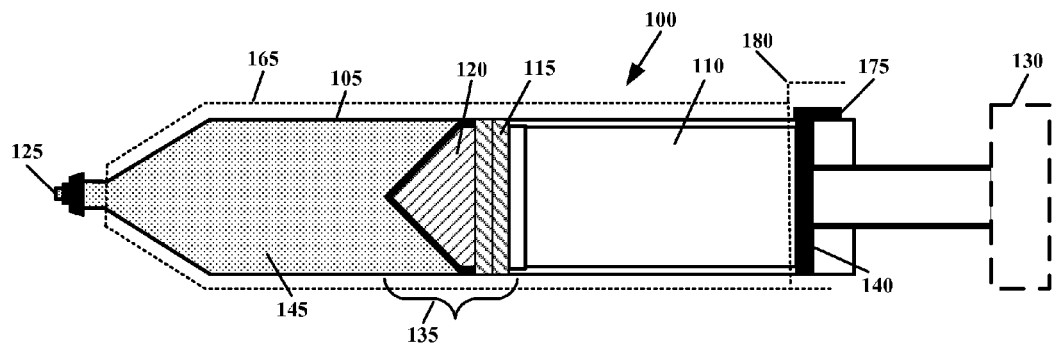
FIG. 1A and FIG. 1B depict an illustrative syringe system according to some embodiments.
Figure 3:
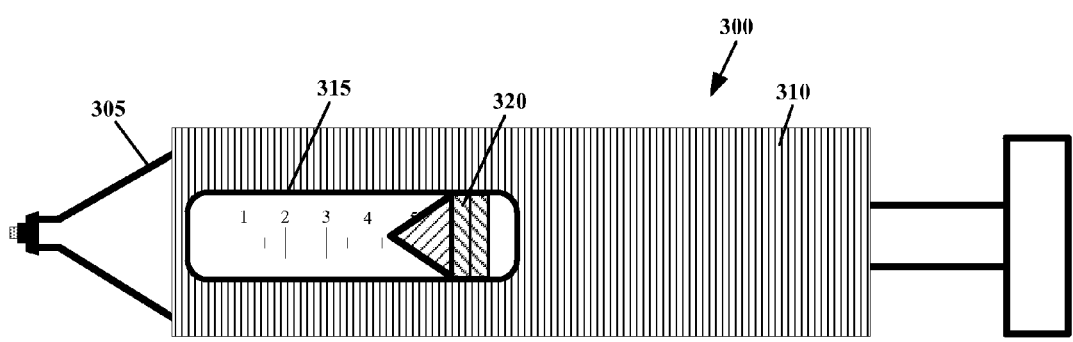
FIG. 3 depicts an illustrative shielded syringe according to some embodiments.

FIG. 1A depicts an illustrative syringe system according to some embodiments. As shown in FIG. 1A, a syringe system 100 may comprise a syringe body 105 having an injector piston 110 arranged therein. The syringe system may further comprise a shield 150, described in more detail below. In FIG. 1A, the shield is depicted as transparent, as indicated by the dotted lines, so as not to obstruct the view of the other components of the syringe system 100. However, the syringe shield is generally not transparent, as illustrated in FIG. 3. The syringe body 105 may be formed in various shapes, including, without limitation, cylindrical, rectangular, and triangular. The syringe body 105 is configured to house a liquid 145, such as a liquid medication or contrast agent, for delivery to a patient through a discharge outlet 125. The syringe body 105 may be comprised of various materials, including, without limitation, glass, metal, polyethylene terephthalate (PET), PET polyester material, polyethylene, polypropylene, acrylic, and polycarbonate.

In general, the injector piston 110 is pushed by an end member 140 located at a proximal end of the injector piston by an injector 130 toward the discharge outlet 125. As the injector piston 110 progresses in a direction away from the injector 130 and toward the discharge outlet 125, the injector piston generates an expulsion force that expels the liquid 145 out of the discharge outlet 125. According to some embodiments, the injector 130 may be a manual injector (e.g., a clinician physically pushing the injector piston 110 with his hand) or an automated injector system (e.g., Spectris Solaris® EP MR Injection System or Stellant® Sx CT Injection System provided by Medrad®, Inc.).

The injector piston 110 may include a plunger 135 arranged at a proximal end thereof. The plunger 135 may comprise a plunger cover 120 and a plunger base 115. In an embodiment, the plunger cover 120 and/or plunger base 115 may comprise rubber, such as natural rubber, silicone, polyethylene, a thermoplastic elastomer, and variations and combinations thereof known to those having ordinary skill in the art. Some embodiments provide that the plunger cover 120 may have a general conical shape, for instance, to correspond with a general conical taper of the distal end of the syringe body 105. The plunger cover 120 and/or plunger base 115 may operate to form a slidable seal with the inner wall of the syringe body 105. In this manner, as the plunger 135 is pushed toward the discharge outlet 125, the plunger forces the liquid 145 toward the discharge outlet and out of the syringe body 105 of the syringe system 100.

Figure 1B:
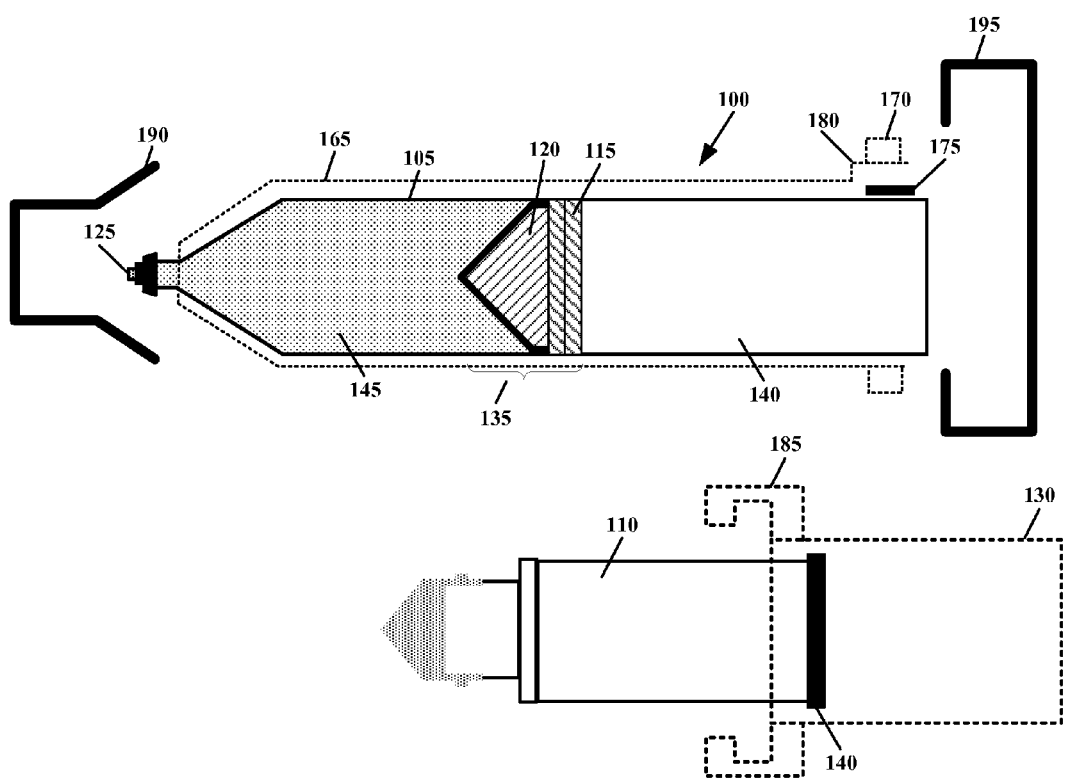

As depicted in FIGS. 1A and 1B, some embodiments provide that the syringe system 100 may comprise a shield 165. For example, the shield 165 may be configured to absorb, block, or otherwise reduce radiation exposure from radioactive drugs (e.g., radiopharmaceuticals) stored in the syringe body 105 to people or equipment.

According to some embodiments, the syringe body 105 preferably contains a syringe alignment structure 175, which may serve one or more purposes, such as orientating the syringe body 105 into a specific orientation with respect to the shield 165, preventing rotation of the syringe body 105 within the shield 165, encoding information about the syringe or its contents, and/or ensuring that the proper syringe is used with the proper shield and vice-versa. Non-limiting examples of syringe alignment structures 175 include tabs, teeth, slots, grooves, or other similar protruding structures. The shield 165 may comprise one or more shield alignment structures 180 (depicted in FIG. 1B) configured to fit over and connect with the syringe alignment structure 175 such that the shield will maintain alignment when installed onto the syringe body 105.

The following embodiments refer to the syringe body 105, shield 165, and components associated therewith depicted in FIG. 1A and FIG. 1B. In one embodiment, if the syringe alignment structure 175 is a tab, then shield mechanical feature 180 may be a groove configured such that mechanical rotation of the syringe with respect to the shield is prevented. In another embodiment, if the syringe alignment structure 175 is a tab, the shield alignment structure 180 may comprise a bayonet (push and turn) groove in the inside of the shield. This arrangement may operate to hold the syringe against accidental rotation and linear displacement. In a further embodiment, the syringe alignment structure 175 and shield alignment structure 180 may be on different parts of the shield 165 and the syringe body 105. For example, shield alignment structures 170 (shown in FIG. 1B), 180 and syringe alignment structure 175 can be at the tip or discharge or distal end of the syringe body 105, or at the proximal end of the syringe body 105 and shield 165. For instance, the back or distal most edge of the syringe body 105 can have a cut-out forming a syringe alignment structure 175 and the shield 165 can have a shield alignment structure 180 which extends inward and fits into the cut-out syringe alignment structure 175 of the syringe body. In a still further embodiment, the syringe body 105 may be free to rotate within the shield 165, but is held in place in the shield by cooperation of shield alignment structure 180 and syringe alignment structure 175 so that it cannot unintentionally slide out of the shield. In yet another embodiment, the shield 165 and syringe body 105 are mounted onto an injector as a single unit. For example, mounting may be accomplished using shield alignment structure 170 to go into a bayonet mount slot arrangement 185 on the front of the injector, similar to bayonet mounts, such as the mounts used on the Spectris Solaris® EP MR Injection System or Stellant® Sx CT Injection System. In this embodiment, the syringe is trapped and held in the system. Alternatively, the shield 165 can be mounted to the syringe body 105 via syringe alignment structure 175 and a syringe alignment structure similar to shield alignment structure 180 that enables the syringe to be mounted on the injector, with the syringe holding the shield in place.

FIG. 1B depicts another illustrative syringe system according to some embodiments. As shown in FIG. 1B, a syringe system 100 may comprise a syringe body 105 having a plunger 135 arranged therein. The syringe body 105 is configured to house a liquid 145, such as a liquid medication or contrast agent, for delivery to a patient through a discharge outlet 125. The syringe body 105 may be enclosed within a shield 165, described in more detail in reference to FIG. 3, below and elsewhere herein. The syringe body 105—plunger 135 configuration may be stored, with or without the liquid 145, until it is needed to deliver the liquid 145 to a patient. According to some embodiments, the plunger 135 of the syringe body 105—plunger 135 configuration may be attached to an injector piston 110, such as described in reference to FIG. 2. For instance, the injector piston 110 may be part of an automatic injection or infusion system 130, such as those described in reference to FIG. 1 (e.g., Spectris Solaris® EP MR Injection System or Stellant® Sx CT Injection System provided by Medrad®, Inc.). The automatic injection or infusion system 130 may operate to push the injector piston 110 and, therefore, the plunger 135 toward the discharge outlet 125. As the injector piston 110 progresses in a direction away from the automatic injection or infusion system 130 and toward the discharge outlet 125, the injector piston generates an expulsion force that expels the liquid 145 out of the discharge outlet. Optionally, the automatic injection or infusion system 130 may operate to pull the injector piston 110 to retract the plunger 135 which can be used to pull fluids into the syringe body 105, for example, to fill the syringe for subsequent use.

Figure 2:
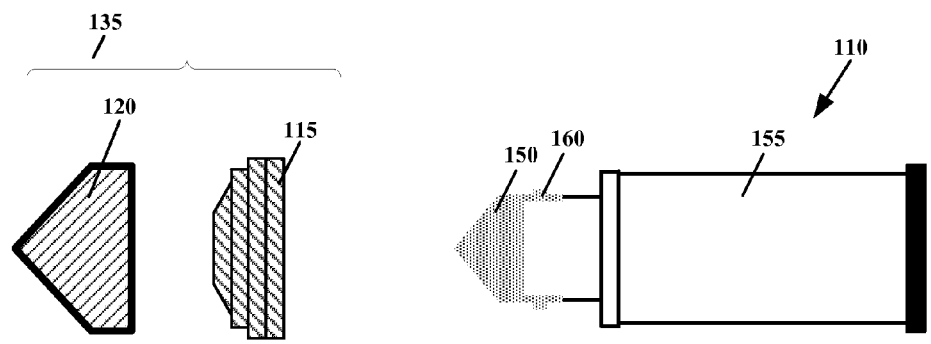
FIG. 2 depicts an illustrative view of some components of a syringe system according to some embodiments.

FIG. 2 depicts an illustrative view of some of the components of a syringe system according to some embodiments. As shown in FIG. 2, the injector piston 110 may comprise an injector piston body 155 having a piston head 150. The plunger 135 may comprise a plunger cover 120 configured to receive a plunger base 115. According to some embodiments, the plunger cover 120 and the plunger base 115 may be interconnected by means of a mechanical connection. A non-limiting example of a mechanical connection includes a bayonet-type, interlocking mechanism. Alternatively, the plunger cover 120 and the plunger base 115 may be assembled into a single piece. The plunger base 115 may be connected to the injector piston body 155 of the injector piston 110 through the piston head 150, for instance, through a mechanical connection. In FIG. 2, the piston head 150 includes a pair of extending flanges 160 and the plunger base 115 may comprise a pair of retaining flanges (not shown). To connect the plunger 135 and the injector piston body 155, the extending flanges 160 on the piston head 150 are inserted into the plunger base 115. When the extending flanges 160 clear the retaining flanges, either the plunger base 115 or the injector piston body 155 is rotated to cause the retaining flanges to be captured behind the extending flanges. To disconnect the plunger base 115 from the piston head 150, the steps may be performed in reverse. In an embodiment, the extending pins or flanges 160 can be withdrawn under the control of the injector 130. For example, through an automatic or manual actuator or other similar device configured to contact, depress, or otherwise disengage the extending flanges 160.

Health care providers need to be protected from certain liquids administered through a syringe. For example, some diagnostic imaging procedures, such as positron emission tomography (PET) and single-photon emission computed tomography (SPECT), require that a patient receive radioactive contrast agents, also called radiopharmaceuticals, to obtain images. Illustrative and non-restrictive examples of radiopharmaceuticals include $^{64}$Cu diacetyl-bis(N4-methylthiosemicarbazone) (e.g., ATSM or Copper 64), $^{18}$F-fluorodeoxyglucose (FDG), Na$^{18}$F (sodium fluoride), 3'-deoxy-3'-[$^{18}$F]fluorothymidine (FLT), $^{18}$F-fluoromisonidazole (FMISO), gallium, technetium-99m, indium-113m, strontium-87m, and thallium. One method for protecting healthcare providers that come into contact with syringes containing radioactive contrast agents and other radioactive substances is to provide a shield around the body of the syringe. In general, a syringe shield is configured to significantly absorb or block radiation from exiting the syringe and contacting a health care provider during handling and/or administering of the radioactive substance.

FIG. 3 depicts an illustrative shielded syringe according to some embodiments. As shown in FIG. 3, a syringe system 300 may comprise a syringe body 305 covered by a syringe shield 310. A window 315 may be arranged in the syringe shield 310 to provide a limited view of the syringe system 300, such as the injector piston 320. In general, once a syringe has been filled with a radioactive substance and has been shielded, the syringe is preferably not removed until the syringe contents have been expelled or otherwise deemed safe (e.g., radioactivity of the liquid is below a predetermined threshold determined based on the life span of the liquid). As such, it would be beneficial to be able to measure one or more properties of the contents of a shielded syringe without having to remove the shield.

The syringe shield 310 may be manufactured out of various materials, including, without limitation, lead, depleted uranium, tungsten, and tungsten impregnated polymers, while the window 315 may be manufactured out numerous types of materials, including, but not limited to, lead glass or lead loaded acrylic. The syringe shield 310 may operate to shield a health care provider, particularly the hands of a health care provider, from radiation emanating from radioactive substance contained within the syringe body 305 as they handle and administer the radioactive substance.

Figure 4:
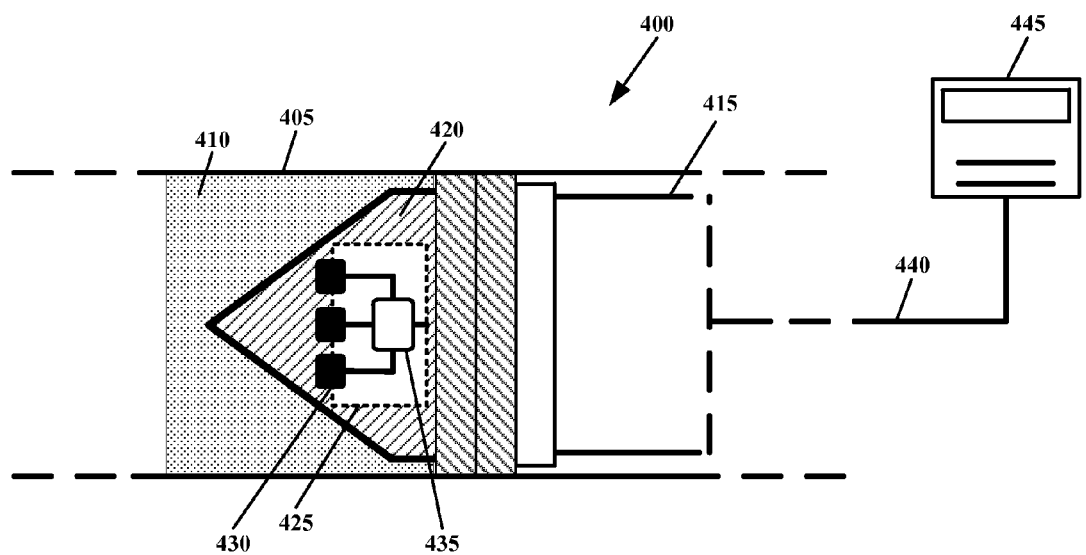
FIG. 4 depicts an illustrative information sensing syringe system according to a first embodiment.

FIG. 4 depicts an illustrative information or property sensing syringe system according to a first embodiment. As shown in FIG. 4, a syringe system 400 may comprise, among other things, an injection piston 415 connected to a plunger 420. The injection piston 415 may be arranged within a syringe body 405 partially filled with a liquid 410, such as a liquid medicine or contrast agent. The plunger 420 may comprise one or more sensors 430 configured to measure one or more properties associated with the liquid 410.

In an embodiment, at least one of the one or more sensors 430 may be located entirely or substantially entirely on an external surface of the plunger 420, in contact with the liquid 410. In another embodiment, at least one of the one or more sensors 430 may be partially integrated into the body of plunger 420, with a portion of the one or more sensors protruding out of the plunger to contact the liquid 410. In a further embodiment, at least one of the one or more sensors 430 may be positioned within the plunger 420 such that it does not contact the liquid 410. For example, the one or more sensors 430 may be configured to measure a property of the liquid 410 without contacting the liquid, such as the radioactivity or electrical conductivity of the liquid. In a further embodiment, the one or more sensors 430 may be partially or fully integrated into the piston head 150 of FIG. 2. In such a configuration, the sensors 430 may be used with multiple syringes and the one or more aspects of the plunger 420 optionally provide a sterile barrier to separate the sensors 430 from contact with the fluid. For instance, if the sensor has to contact the fluid to make a desired measurement, then the sensor may be configured as part of the plunger 420, which is disposed after each use to reduce cross contamination. If the sensor does not need to contact the fluid to make a measurement, such as when measuring ionizing radiation, then all or substantially all of the sensor may be incorporated into the piston head 150 or other aspect of the injector, for instance, so that it can be used multiple times.

Although FIG. 4, and FIGS. 5-7 described below, depict a sensor (e.g., one or more sensors 430) in a particular position within a syringe and/or injector piston embodiments are not so limited, as the location of sensors in any position that may operate according to embodiments described herein are contemplated in this detailed description. For example, an embodiment provides that the sensors 430 may comprise a plurality of sensors arranged at various locations within the syringe system 400, such as the plunger 420 and/or the injector piston 415. The sensors 430 may be redundant sensors (e.g., the same type of sensor and/or configured to measure the same property of the liquid 410) and the syringe system 400 may be configured to use the sensors to check the accuracy of the measurement of one or more properties of the liquid 410. For instance, the sensors 430 may comprise two radioactivity sensors located at different locations on the plunger 420. The syringe system 400, such as through a logic device 445, may operate to compare measurements from the two sensors 430 to determine whether their measurements coincide (e.g., within a threshold range). If the measurements do not coincide, the syringe system 400 may generate an alert or otherwise respond to the condition that the measurements at the different sensors 430 do not match.

The one or more sensors 430 may be configured to detect and/or measure one or more properties associated with the liquid 410. According to some embodiments, the one or more properties may include, without limitation, pH, temperature, salinity, viscosity, radioactivity, radiation absorptivity, voltage, conductivity, analyte concentration, optical characteristics, pressure, and combinations thereof. In an embodiment, the one or more sensors 430 may operate to measure a value of the one or more properties of the liquid, such as a concentration (e.g., about 370 mgI/ml) or radioactivity (e.g., about 10 mCi or about 370 MBq). In another embodiment, the one or more sensors may operate to detect the presence or absence of a condition, such as a property being above or below a threshold or outside or inside a range. For instance, a sensor 430 may operate to detect radiation above a threshold level or a pH below a predetermined value.

Certain properties of a liquid, such as the illustrative properties listed above, may be unchanged during preparation and delivery of the fluid by the injector or fluid delivery system, unless the system has the ability to dilute, mix or otherwise alter the fluid. Certain other properties may be imposed on the liquid by the injector system or the environment, for example temperature, pressure, movement, or flow. For example, pushing on the piston increases the pressure in the syringe and causes the fluid to flow if the syringe is not capped. Without a source of pressure, the fluid has no pressure itself except for pressure due to the effects of gravity and air pressure. Furthermore, when the injector is pressurizing the system and fluid is flowing, the pressure and velocity may be different in different fluid path elements or parts. Similarly, in an example system in which the fluid flows through a heater or a heat loss element, the temperature will be different in different parts of the fluid. Still other properties of the liquid, such as viscosity, depend upon temperature and, for some fluids, pressure, flow, and/or shear. In a further example, injectors may include heaters to maintain the temperature of a liquid, for instance, to keep the viscosity low and increase the patient's comfort. A non-limiting example provides for a an injector including one or more pressure measuring devices comprising a sensor to detect the force upon at least a portion of a contact surface of a syringe plunger during pressurization of a fluid medium within the syringe. In this manner, a determination of the pressure of the fluid medium within the syringe may be achieved.

Referring again to FIG. 4, the one or more sensors 430 may be operatively coupled to a sensor device 435 configured to receive data from the one or more sensors 430. The sensor device 435 may be arranged within the plunger 420, shown through cut-out 425 indicated by the dotted line. For instance, the one or more sensors 430 may contact the liquid 410 and provide data (e.g., conductivity) to the sensor device 435, and the sensor device may process the data to provide information about at least one of the one or more properties (e.g., concentration).

According to some embodiments, the syringe system 400 may be communicatively coupled to a logic device 445, for instance, through a communication pathway 440 that extends from the one or more sensors 430 and/or the sensor device 435, through the injector piston 415, and out through the proximal end (not shown) (e.g., a plunger rod, the end member 140 or injector 130 of FIG. 1A and/or FIG. 1B, a connection to an automatic injector system such as in FIG. 1B, etc.) to the logic device. Some embodiments provide that the communication pathway may comprise various communication methods and protocols, including serial, parallel, universal serial bus (USB), Ethernet, wireless (see FIG. 5), combinations thereof, and any other communication method and/or protocol in existence or developed in the future that is capable of supporting communication according to embodiments described herein. In an embodiment, the logic device 445 may be in communication with one or more networks and/or health information systems, such as a picture archiving and communication system (PACS).

In an embodiment, the logic device 445 may comprise an electronic display device configured to display information received from the one or more sensors 430. For example, the logic device 445 may comprise a digital display, such as an LCD display, attached to the syringe system 400 (e.g., attached to the syringe body 405 or a shield encasing the syringe body) and configured to present numerical values relating to the information from the one or more sensors 430 (e.g., concentration values, radioactivity values, etc.).

Although the one or more sensors 430 are depicted in FIG. 4 as being connected to a sensor device 435, embodiments are not so limited, as the one or more sensors may be communicatively coupled directly to the logic device 445 or may not be coupled to a sensor device 435, logic device 445, or any other electronic device or element. For example, in an embodiment, the one or more sensors 430 may be configured to communicate to the injection system 130 directly or to an operator of the syringe system information about the one or more properties. In such an embodiment, the one or more sensors 430 may be configured to generate a visible and/or audible signal conveying information about the properties (e.g., changing color at a certain pH level, turning on an LED light below a threshold radioactivity level, etc.). In addition, or alternatively, the sensors 430 may provide the measurement to the injection system 130 for operational actions. For example, the injection system 130 may be configured to generate a visible and/or audible signal conveying information about the properties based on measurement information received from the one or more sensors 430.

In an illustrative and non-restrictive example involving delivery of a radioactive agent to a patient, the operator of a syringe system configured according to embodiments described herein will want to administer an amount of radioactivity. Given radioactive decay, setting the radioactivity to be delivered will be used to determine the volume to be injected, given a known syringe size, plunger position, and the concentration or total dose of radioactivity in the syringe. As such, an automatic injector using a syringe system configured according to some embodiments will automatically determine, based on sensing the radioactivity in the syringe using the one or more sensors, what volume to inject.

The logic device 445 may be a computing device, such as a mobile computing device (e.g., smart phone, tablet computing device, etc.), laptop, server, or personal computer (PC), or an automatic injector system (such as 130 depicted in FIG. 1B) configured to receive information from the syringe system 400. The logic device 445 may comprise one or more processors and system memory (not shown), such as the computing device 800, processor 804 and system memory 806 depicted in FIG. 8 below. According to some embodiments, the logic device 445 may be associated with software configured to manage and/or control the syringe system 400, associated data, and components thereof as described herein. For example, the logic device 445 may be configured to initiate an event if a property is outside of allowable limits. Illustrative and non-restrictive examples of events include generating an alarm or other communication, preventing injection of the liquid 410, ejecting the syringe from an automatic injection system, and combinations thereof.

Figure 5:
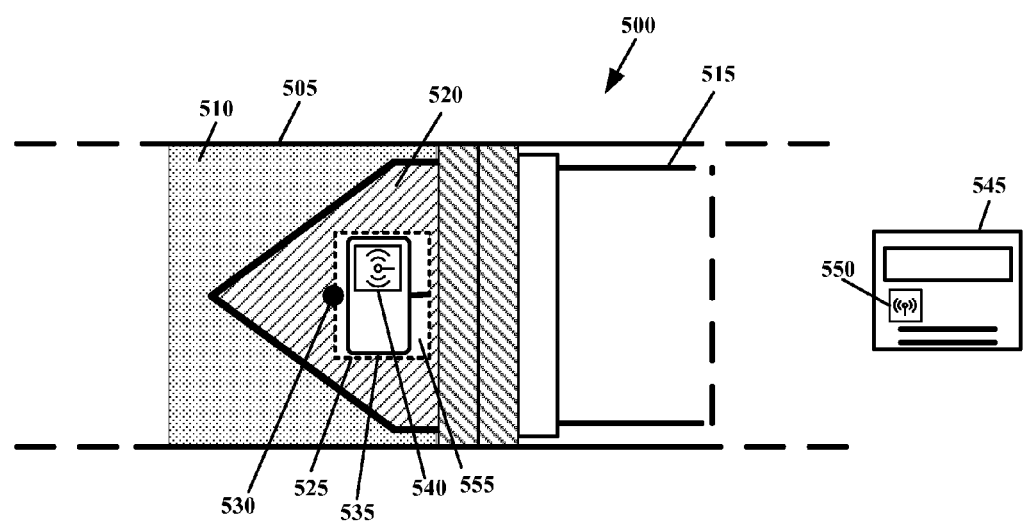
FIG. 5 depicts an illustrative information sensing syringe system according to a second embodiment.

FIG. 5 depicts an illustrative information sensing syringe according to a second embodiment. As shown in FIG. 5, a syringe system 500 may include an injection piston 515 connected to a plunger 520 located at a distal end thereof. The injection piston 515 may be arranged within a syringe body 505 partially filled with a liquid 510. The plunger 520 may have one or more openings 530 configured to allow a portion of the liquid 510 to enter a cavity 555 arranged within the plunger, shown through cut-out 525 indicated by the dotted lines. A sensor 535 may be located in the cavity 555 such that the sensor may contact or interact with the liquid 510 entering the cavity to measure and/or detect one or more properties thereof. According to some embodiments, the one or more openings 530 may comprise inlets in the plunger 520 or may comprise a porous or semi-permeable membrane that allows the liquid 510 to enter the cavity 555. In the second embodiment of FIG. 5, the sensor 535 may comprise a wireless transceiver 540 configured to wirelessly transmit information, such as information associated with the one or more properties of the liquid 510 in the cavity 555, to a logic device 545 having a wireless transceiver 550.

In an embodiment, the volume of liquid 510 entering the cavity 555 may be known such that the amount of liquid available for injection into the patient may be adjusted accordingly. For example, the syringe system 500 may be calibrated (e.g., syringe graduations, automated volume determinations, etc.) such that the volume of liquid 510 entering the cavity 555 will be subtracted from the volume of liquid available for injection into the patient through the syringe system.

Figure 6:
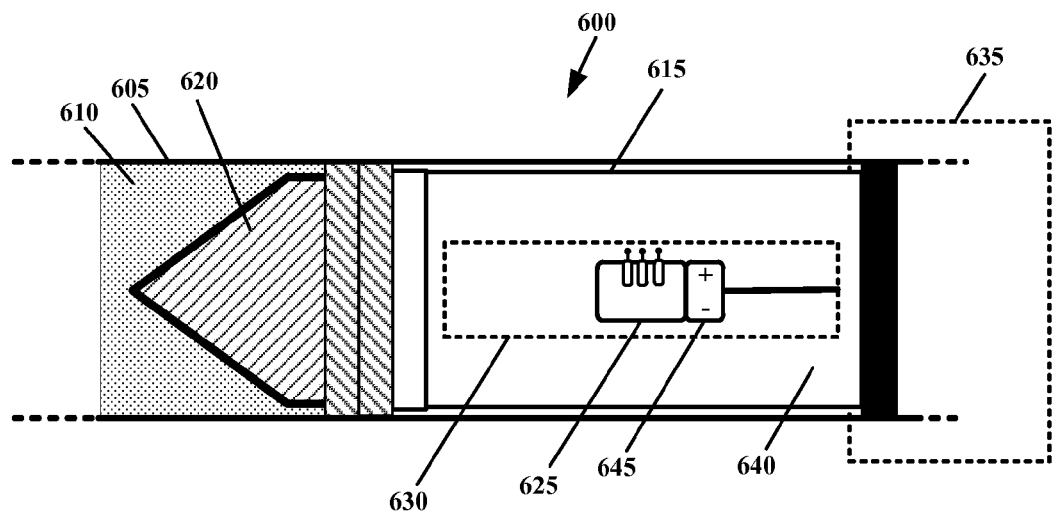
FIG. 6 depicts an illustrative information sensing syringe system according to a third embodiment.

FIG. 6 depicts an illustrative information sensing syringe according to a third embodiment. As shown in FIG. 6, a syringe system 600 may include an injection piston 615 connected to a plunger 620 located at a distal portion thereof. The injection piston 615 may be arranged within a syringe body 605 partially filled with a liquid 610. The injector piston 615 may have one or more sensors 625 arranged therein, as shown through cut-out 630 indicated by the dotted line. The one or more sensors 625 may be configured to detect and/or measure one or more properties associated with the liquid 610. As shown in FIG. 6, it is not necessary that the one or more sensors 625 contact the liquid 610 in order to measure and/or detect properties associated with the liquid. For example, at least one of the one or more sensors 625 may comprise a radiation sensor capable of measuring and/or detecting radiation of the liquid 610 without contacting the liquid. The injector piston 615 may be part of an automatic injector system 635 configured to manage and control the delivery of the liquid 610 to a patient.

According to some embodiments, the one or more sensors 625 may be communicatively coupled to an electronic device, logic device, computing device, or combinations thereof, for example, for processing and/or displaying the information from the one or more sensors and/or the sensor device. As shown in FIG. 6, the one or more sensors 625 may be electronically coupled to a power source 645 configured to provide power thereto. In the embodiment depicted in FIG. 6, the power source 645 may be located within the syringe system 600, such as in the injector piston body 640. A non-limiting example provides that the power source 645 may be a battery.

Figure 7:
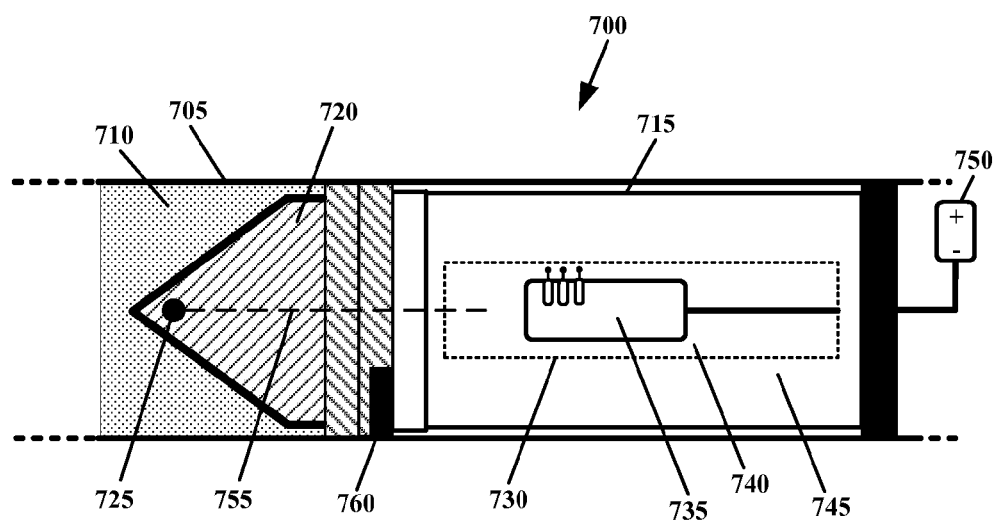
FIG. 7 depicts an illustrative information sensing syringe system according to a fourth embodiment.

FIG. 7 depicts an illustrative information sensing syringe according to a fourth embodiment. As shown in FIG. 7, a syringe system 700 may include an injection piston 715 connected to a plunger 720 located at a distal end thereof. The injection piston 715 may be arranged within a syringe body 705 partially or fully filled with a liquid 710. The plunger 720 may be in fluid communication with a cavity 740 arranged within the injection piston body 745, shown through cut-out 730 indicated by the dotted lines. As such, a portion of the fluid 710 may enter the cavity 740 through one or more openings 725 in the plunger 720.

In an embodiment, the fluid 710 may enter through a measurement path 755 within the plunger 720. The measurement path 755 is a part of the plunger 720 or the whole plunger which has properties to match up to the injection piston 715 to provide a pathway for information containing phenomena, for example, light or electrical current, to the sensor 735 for sensing or measurement. For example, the measurement path 755 may be configured as a clear or light transmitting segment when the sensor 735 measures light. Alternatively the measurement path 755 may be configured as a wire if the sensor 735 measures current or voltage. In some embodiments, the measurement path 755 can act to affect, limit or control the transmitting of the information containing phenomena. In these embodiments, the measurement path 755 may comprise, for example, a narrow light pipe configured to focus the light going into the syringe or an energy absorbing or focusing filter if sensing ionizing radiation sensing.

According to some embodiments, it is necessary to align the plunger 720 with the piston body 745 and/or the sensor 730 through an alignment feature (not shown) such as the tab 175 used on syringe body 105 in FIG. 1. Alternatively, alignment can be accomplished by aligning the plunger 720 with the syringe body 705 when manufactured or otherwise before use so that sufficient alignment is achieved by aligning syringe body 705 with the piston 715, for example, through the shield, the injector, or directly.

According to some embodiments, such as when measuring ionizing radiation, because the radiation generally penetrates the piston material, the piston is made consistent from syringe to syringe. In some embodiments, the piston 715 may contain a coding mechanism 760 for communicating with the sensor 735 or a computing device of the existence of or information about any piston properties relevant to the measurement being made. Examples of coding mechanisms 760 include, but are not limited to, physical indicia, labels, or electronic tags such as RFIDs. A sensor 735 may be arranged within the injection piston body 745 to contact at least a portion of the liquid 710 in the cavity to measure and/or detect one or more properties of the liquid. According to some embodiments, the one or more openings 725 may comprise inlets in the exterior of the plunger 720 or may comprise a porous or semi-permeable membrane that allows the liquid 710 to enter the cavity 740.

As shown in FIG. 7, the one or more sensors 735 may be electronically coupled to a power source 750 configured to provide power thereto. In the embodiment depicted in FIG. 7, the power source 750 may be located external to the syringe system 700. For example, a wire or wires configured to carry electric power may extend outside of the syringe system 700, such as through the end of the injector piston 715 (e.g., through an opening in a plunger rod (not shown)) and connect to a power source 750. The power source may be a battery, outlet power source (e.g., AC power outlet), or an electronic device (e.g., a computing device, automatic injector system, etc.). In one embodiment, power may be coupled to or through the plunger rod magnetically.

Embodiments are not limited to the power source configurations depicted in FIGS. 6 and 7 as these are non-restrictive embodiments provided for illustrative purposes. The sensors, sensor devices, and any associated electronic elements may be powered using suitable power sources capable of powering sensors provided according to embodiments described herein. For example, a power source may be located in various other parts of the syringe, such as the plunger and/or plunger rod. In another example, the power supply may comprise an automatic injector system. For instance, a sensor may be arranged within a piston connected to an automatic injector system configured to supply power to the sensor.

As depicted in each of FIGS. 4-7, any portion, including all or substantially all of the injector piston, may be used to contain sensors and/or sensor devices. In this manner, sensors and/or sensor devices of various sizes and dimensions may be accommodated in a syringe system configured according to embodiments described herein. In an embodiment, a sensor may be arranged along the entire length or substantially along the entire length of the injector piston, including the plunger and the injector piston body, as well as portions of the injector piston external to the syringe body of the syringe, such as a plunger rod. As such, the sensor, and any associated elements (e.g., sensor devices, wires, power sources, etc.) may be located within a syringe system provided according to some embodiments described in this detailed description.

According to some embodiments, the sensor may be arranged within the piston injector only, which is a part of an automatic injector system. In this manner, an automatic injector system may sense and/or measure one or more properties of a liquid contained in a syringe connected to the automatic injector. There is a cost benefit to embodiments which use the sensor for multiple syringes. If the sensor needs to contact the fluid to make a measurement, there is a sterility benefit to embodiments providing a new sensor or fluid contact path or element with each syringe.

As depicted in FIGS. 4 and 5, some embodiments provide that the sensors and/or sensor systems may be connected to a logic device, such as a computing device or an electronic medical device (e.g., automatic injector system). In an embodiment, the information from the sensors and/or sensor systems may be transmitted directly, through a computing device, through an electronic medical device, and combinations thereof to one or more databases and/or health information systems including, but not limited to, a picture archiving and communication system (PACS), a healthcare information and management systems (HIMS), an electronic medical record (EMR) systems, a radiology information systems (RIS), a contrast information management systems, and a medical imaging and procedure equipment information systems (e.g., contrast injector systems or computed tomography (CT) scanners). Some embodiments provide that the sensor and/or sensor device may be in communication with various other information platforms, such as the Medrad, Inc. Certegra™ Informatics Platform.

The embodiments depicted in FIGS. 4-7 are illustrative and non-restrictive. A syringe system configured according to embodiments described herein may include more or fewer components than those depicted in FIGS. 4-7. In addition, the components may be arranged in various arrangements and/or positions.

Some embodiments provide that the sensors may comprise radiation sensors, pH sensors, optical sensors, analyte sensors, concentration sensors and combinations thereof. In an embodiment, a sensor may be modified to operate within the syringe system. For example, certain structural elements of a sensor may be modified to fit within the available space of a particular syringe component, to protrude through the plunger and contact the liquid within the syringe, to operate under various radiation protection (RP) protocols, to be coated with one or more materials, for instance, to prevent reactions or other interactions between the sensor components and the liquid, or combinations thereof. According to some embodiments, the sensors may comprise silicon diodes, avalanche diodes, scintillators, photomultipliers, solid state crystals, semiconductors, Geiger tubes and combinations thereof. Additional illustrative sensors include, without limitation, silicon PIN diode radiation sensors, ionization-chamber radiation detectors, silicon photodiodes, microdischarge-based radiation detectors, sodium iodide crystal radiation detectors, bismuth tri-iodide crystal radiation detectors, or cadmium tellurium and cadmium zinc tellurium semiconductor crystal radiation detectors. In a non-restrictive example involving a radiation sensor, such as a light-emitting crystal-based radiation sensor, the radiation sensor will be associated with a photosensor.

According to some embodiments, a sensor may comprise a micro sensor, such as a sensor associated with an integrated circuit. A micro sensor or MEMS may be generally configured to provide sensing capability (e.g., concentration, radioactivity etc.) in a form capable of being integrated into smaller spaces, such as a syringe or injector piston and components thereof.

Figure 8:
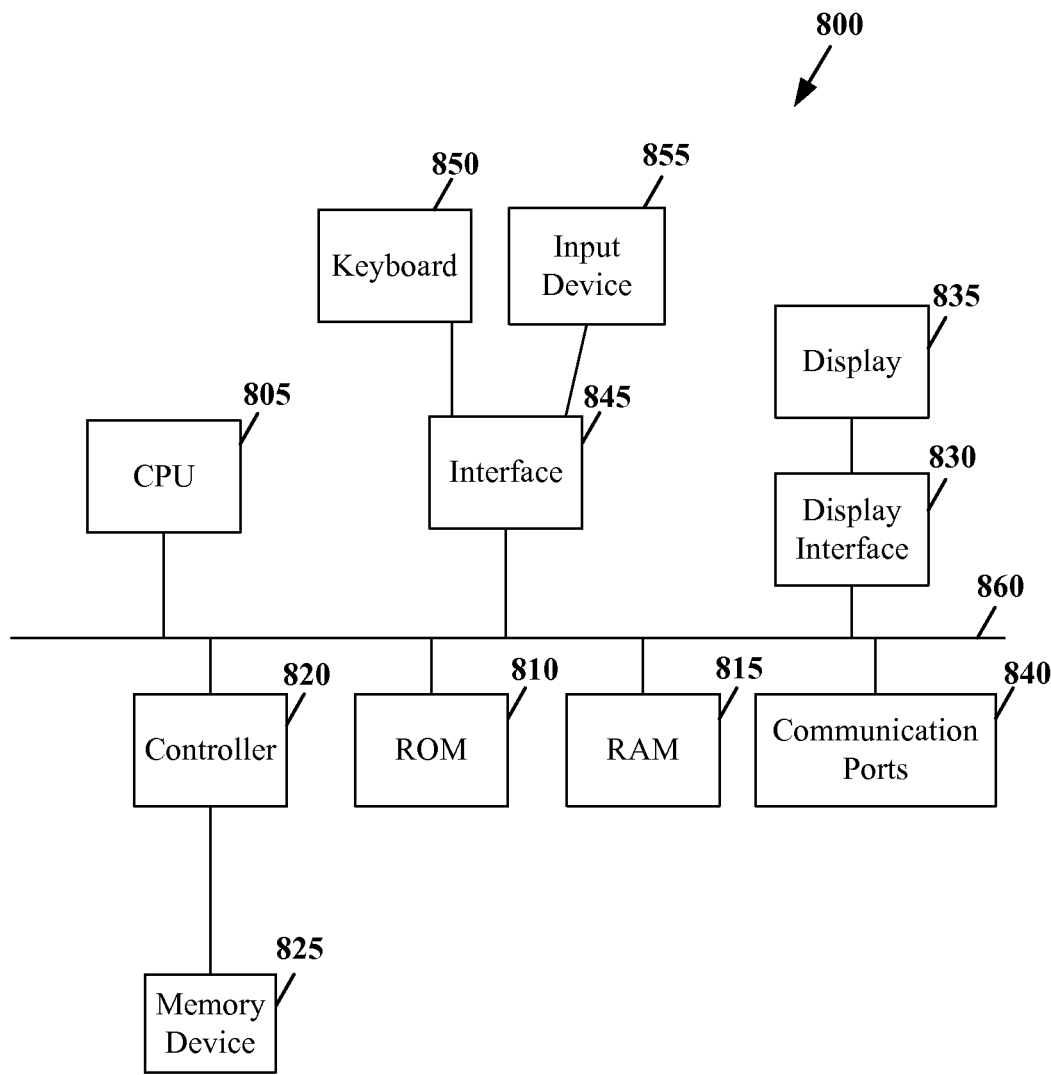
FIG. 8 depicts illustrative computing device internal hardware according to some embodiments.

FIG. 8 depicts illustrative computing device internal hardware according to some embodiments that may be used to receive information from sensors described herein, to process and/or display sensor information, contain or implement program instructions relating the sensor information, and combinations thereof. The computing device 800 may include a bus 860 serves as the main information highway interconnecting the other illustrated components of the hardware. CPU 805 is the central processing unit of the system, performing calculations and logic operations required to execute a program. CPU 805, alone or in conjunction with one or more of the other elements disclosed in FIG. 8, is an exemplary processing device, computing device or processor as such terms are used within this disclosure. Read only memory (ROM) 810 and random access memory (RAM) 815 constitute exemplary memory devices (i.e., processor-readable non-transitory storage media).

A controller 820 interfaces with one or more optional memory devices 825 to the system bus 860. These memory devices 825 may include, for example, an external or internal DVD drive, a CD ROM drive, a hard drive, flash memory, a USB drive or the like. As indicated previously, these various drives and controllers are optional devices.

Program instructions, software or interactive modules for providing the interface and performing any querying or analysis associated with one or more data sets may be stored in the ROM 810 and/or the RAM 815. Optionally, the program instructions may be stored on a tangible computer readable medium such as a compact disk, a digital disk, flash memory, a memory card, a USB drive, an optical disc storage medium, such as a Blu-Ray™ disc, and/or other non-transitory storage media.

An optional display interface 830 may permit information from the bus 860 to be displayed on the display 835 in audio, visual, graphic or alphanumeric format. Communication with external devices, such as a print device, or other or other may occur using various communication ports 840. An exemplary communication port 840 may be attached to a communications network, such as the Internet or an intranet.

The hardware may also include an interface 845 which allows for receipt of data from input devices such as a keyboard 850 or other input device 855 such as a mouse, a joystick, a touch screen, a remote control, a pointing device, a video input device and/or an audio input device.

In one of the embodiments, computing device 800, which may be integrated with or be a part of an injector system (e.g., automatic injector system 130 depicted in FIGS. 1A and 1B), receives information about at least the position of the plunger in the syringe and the measurement of at least one sensor. For some properties of a well-mixed fluid, for example pH, measuring the property in a small volume of the fluid allows knowledge of the property in the whole volume. For other properties, such as radiation dose, because the penetrating radiation is partially transmitted, partially scattered, and partially absorbed by intervening fluid, and because the response of the sensor to a particular volume or voxel in space is spatially dependent, even if the fluid has a uniform concentration of the radiopharmaceutical, the measurement of a sensor in the plunger or piston tip will be a convolution or integral of the geometric response and the fluid concentration and, thus, may depend upon position.

A non-limiting first example includes a syringe filled with a radioactive contrast agent for a positron emission tomography (PET) or single-photon emission computed tomography (SPECT) scan. The radioactive contrast agent will be prepared by a nuclear pharmacy facility and delivered to a health care facility at 8:00 a.m. The PET or SPECT scan will be scheduled for 9:00 a.m. An injector system having a silicone diode radiation sensor arranged within the piston will be filled or mated with the syringe with the radioactive contrast agent. The syringe will be shielded with a lead syringe shield, optionally having a lead glass window. The syringe, shield, injector, and or associated data device will be in communication with a computing device configured to also receive information from the radiation sensor. An operator will view information indicating the radioactivity level of the radioactive contrast agent on a display coupled to the computing device. The operator will set the dosage for the patient and the injection system will deliver the prescribed dose of radioactive contrast agent to the patient based on the information from the sensor accordingly for the 9:00 a.m. PET or SPECT scan.

In a non-limiting second example, if a syringe containing a uniform fluid with about 1 mCi of radioactivity in 1 ml of fluid gives a sensor reading or measurement of about X, then the same syringe containing about 2 mCi of the same radioisotope in the same 1 ml will give a sensor measurement of about 2X. However, that same syringe containing about 2 mCi in about 2 ml of fluid will give a reading of about X', which will, under most geometries and conditions, be less than about 2X. The reading will be less than about 2X because with about 2 ml of fluid in the syringe, the forward most milliliter is farther from the piston or plunger and the measurement of radiation in first principles falls off as 1 over distance squared, although back scatter from the shielding and other materials may have an effect on such measurements. Thus, by using the knowledge about the position of the piston and plunger in the syringe and the geometry and effect shielding materials, the computing device 800, through suitable calibration and software, for example, stored in memory device 825, and operative on CPU 805, may correctly compensate or correct for this variation in the geometric response of the sensor—syringe system.

Further in this second example, if the piston contains a second sensor proximal to the first (that is, a sensor closer to the motor and further from the syringe), with 1 mCi in 1 ml, the second sensor will measure about Y, where Y will most likely be less than about X. With that same syringe containing about 2 mCi of the same radioisotope in the same 1 ml, the second sensor will give a sensor measurement of about 2Y. With that same syringe containing about 2 mCi in about 2 ml of fluid, the second sensor will give a reading of about Y', which will under most geometries and conditions be less than about Y. In addition, because the second sensor is more distant from the fluid than the first, the decrease or fall of its response is more gradual with an increase in fluid volume. Thus Y'/Y will, for most geometries and expected conditions, be greater than X'/X, or equivalently Y'/X' will be greater than Y/X. This ratio of sensor measurements gives an independent measurement. This independent measurement may be used for various purposes, including, without limitation, to confirm fluid uniformity, to check proper functioning of the sensor, and/or to check proper functioning of the injector or its position measurement. Additional independent measurements can be provided by having one or more sensors provide additional measurements to the injector for the computation of radiation dose. For instance, additional sensors may include, but are not limited to, sensors that are associated with a syringe shield, sensors that are part of the injector but slide into the shield next to the syringe, or a combination thereof.

Another embodiment to adjust the response with respect to syringe fill, or what is essentially the same thing, plunger position, may include radiation absorbing elements. One example geometry comprises a tungsten plug with a narrow hole that "looks" down the barrel of the syringe towards the syringe tip. Depending on the width to height ratio of the hole, the energy of the radiation, and the absorptivity of the absorbing material and the drug liquid, this arrangement may operate to improve the linearity of the response. In a further embodiment, different absorbing materials can be placed around or in front of different sensors. When used with multiple sensors, this can enable the computing device to estimate the spectrum or energy of the radiation being measured, with more sensors providing more information about the energy spectrum of the radiation. This information can be used, for example, to further adjust the geometric response or the sensor system and/or to compare with the expected response of the drug that the user has programmed the computing device, such as computing device 800 of FIG. 8, to expect to be in the syringe. The user can be alerted by the system if the dose, the energy spectrum or any other fluid property is not with a predetermined margin of error.

A further embodiment uses at least one absorber, for example a tungsten disk, and two sensors, with the sensors placed generally on the center axis of the piston as shown in FIG. 6 and the absorber placed between the two sensors. This causes one sensor to be more sensitive to radiation coming from inside the syringe and the other sensor to be more sensitive to radiation coming from the outside of the syringe, which could interfere with the accurate measurement by the first sensor of the radiation in the syringe. Thus these two sensors with the known geometry and absorber properties can be used to compensate or correct for external sources of radiation and/or to identify or confirm a that a particular radiopharmaceutical (and concentration thereof) is what was expected. To generalize, multiple sensors with one or more absorbers of known geometry, and/or a sequence of measurement made at different positions may enable the determination of one or more properties of the radiopharmaceutical. Illustrative and non-restrictive examples of properties include uniformity of composition and the presence or absence of air, and the radioisotope(s) involved.

In a still further embodiment, a syringe and/or injection system described herein may be used as a filling system, for instance, to fill one or more syringes with the liquid from another container, such as a bulk source or multi-patient vial. To accomplish this, the syringe tip is generally pointed up so that air will rise and can be pushed out of the tip. The syringe is connected to the bulk source, some fluid is pulled in by pulling the injector piston and, thus, the syringe plunger distally. Then the direction of motion is reversed and any remaining air and optionally a little fluid is pushed from the syringe into the bulk source or a waste container. After this "burping" or purge process to remove any air, the injector piston and syringe plunger are pulled back or more distally to draw liquid into the syringe. As the syringe is being filled, the sensor measures the property of the fluid as it is filling. In the case of radioactivity, the sensor measures radioactivity and knowing the position, can determine that radioactivity in the syringe. When the proper amount has been drawn in, the system can stop the filling process and inform the user that the fill is complete.

In a further embodiment, the operator specifies the desired dose, the isotope or drug being filled, and the time in the future at which that dose is required. The system then computes the dose that needs to be drawn now to provide the desired dose in the future and executes a fill function to accomplish this. In a further embodiment, the computing device 800, through suitable software, for example, stored in memory device 825, and operative on CPU 805, uses two or more data sets, each set including at least the sensor measurement and optionally the position of the piston (and thence plunger), to confirm that the fluid being pulled into the syringe is of a uniform concentration and optionally within limits of expectations set by the user or system. For example, if some air is being pulled in by accident or if air remains from the purge cycle discussed above, because it will tend to collect upward most parts of the syringe, the sensor response will not follow the expected geometric response curve as discussed above. If the deviation is more than some predetermined allowed deviation, the operator is alerted and can take the proper action, for example, looking for bubbles through the lead glass window in the shield. If the fluid being drawn in is non-uniform in concentration, the sensor response versus plunger position will vary, but in a less predictable way, for instance, depending upon whether concentration is increasing or decreasing.

In an additional embodiment, when a prefilled syringe is loaded on to the injector, the injector system or computing device 800, through suitable software, for example, stored in memory device 825, and operative on CPU 805, measures the sensor reading and plunger position. If information about the radiation dose that should be in the syringe has been transmitted either in paper or electronically or via a data device such as label or memory associated with the syringe or shield, the injector system can confirm that what is present in the syringe is within predetermined tolerance limits of expectations set by the user, the pharmacy, system, and or other operator. If it is not, the user can be alerted or the system may not be able to proceed without operator action. If it is within tolerance, use can proceed. The sensor or sensor array or system cannot itself know if the fluid is of a uniform concentration and/or that there are no significant air bubbles. And, if the shield is generally or fully opaque, being commonly made from a dense material, in this case, the computing device 800, through suitable software, for example, stored in memory device 825, and operative on CPU 805, may use two or more data sets acquired, for example, one data set when tipping the injector head so that the syringe tip is up and a second with the syringe tip down, or during two different fill conditions during priming of attached disposable elements or fluid path or during different fill conditions of the injection itself, each set including at least the position of the piston (and thence plunger) and at least one sensor output, to confirm that the fluid being delivered from the syringe is of a uniform concentration and optionally within limits of expectations set by the user, the pharmacy, system, or other operator. If this is not the case the injector system can take action that has been predetermined or programmed by the operator or equipment manufacturer. One example action is to re-compute the concentration and adjust the amount of fluid delivered accordingly. A second example action is to stop injection and alert the operator. A third example action is to continue the injection and alert the operator. A fourth example action is to continue the injection and alert the operator, provided that there is no chance of injecting too much radiation, but to stop the injection if there is a chance of injecting too much radioactivity into the patient. These checks may be done while loading or preparing the system, upon arming of the system, during the injection, and/or the delivery of the fluid.

An additional sensor that could be used by computing device 800 to help ensure safety is a tilt sensor or switch on the head. To use this, the computing device 800, through suitable software, for example, stored in memory device 825, and operative on CPU 805, takes a reading of plunger position and sensor output with the syringe tip pointing up and a second reading with the syringe tip pointing down. If there is no or minimal air, these two readings will be identical within some tolerance. If the difference is greater than that the allowed tolerance, then the system can alert the operator or user that there is air or some other cause of a non-uniform concentration.

Measuring the radiation dose via the plunger in a syringe and optionally using the knowledge of the geometries involved and the output of at least one sensor has a significant benefit to the user. As mentioned herein, it allows the filling of a syringe and the confirmation of the dose in the syringe without the user having to take the syringe out of the shield to measure the total dose of the contents in the dose calibrator. This greatly reduces radiation exposure to the user. In addition, the syringe can be transported in the shield in which it was filled, by, for example, adding radiation protecting caps (190 and 195 in FIG. 1B) to both ends or placing the syringe in the shield into a shielded syringe carrier. Then at the site where the drug is to be administered a patient, the syringe remains in the shield and the shield and syringe are attached to the injector, for example, with matching bayonet mounts or the mounts used for example on the Spectris Solaris® EP MR Injection System or Stellant® Sx CT Injection System as discussed herein. Once the syringe plunger is mated with the injector piston, the injector system can measure the radiation in the syringe, compare the measurement to the expected value, and either be ready for injection or require operator intervention if something is amiss. Thus, there is no need for the operator at the injection site to remove the syringe from the shield to measure or adjust the dose, reducing the likelihood of radiation exposure to the operator. The injector can determine the proper volume and either inject only the volume needed to deliver the desired dose into the patient, with any extra remaining in the syringe for subsequent disposal, or the operator can instruct the injector to deliver the extra dose to a suitable waste container before beginning injection to the patient, so that only the correct amount remains in the syringe. This has the benefit that extra radiation cannot be delivered to the patient.

The benefits of providing a sensing of fluid properties by a sensor in the piston and/or plunger exists whether the plunger and piston are acted upon by a motor or other external drive to move fluid movement or pressurization or when the plunger and piston move in response to positive or negative pressures applied elsewhere in the fluid path or by some other fluid path element. Likewise, the fluid containing function of a syringe with a sliding plunger and the injector piston could be accomplished via various configurations, including, without limitation, a rolling diaphragm, a bellows syringe, or a collapsible syringe/bag with a piston like region that moves, compresses or expands with the fluid container.

Medical fluids, such as radiopharmaceuticals, may be carried through tubing or other fluid delivery channels for injection into a patient. For example, typical automated infusion systems move the fluid using an infusion pump through a delivery tube and into a patient's venous system through a needle or catheter. According to some embodiments, a fluid delivery channel flow control system may be configured to control the flow of and/or measure one or more properties of a fluid within the tubing of a fluid delivery system (e.g., automated injector system).

Figure 9:
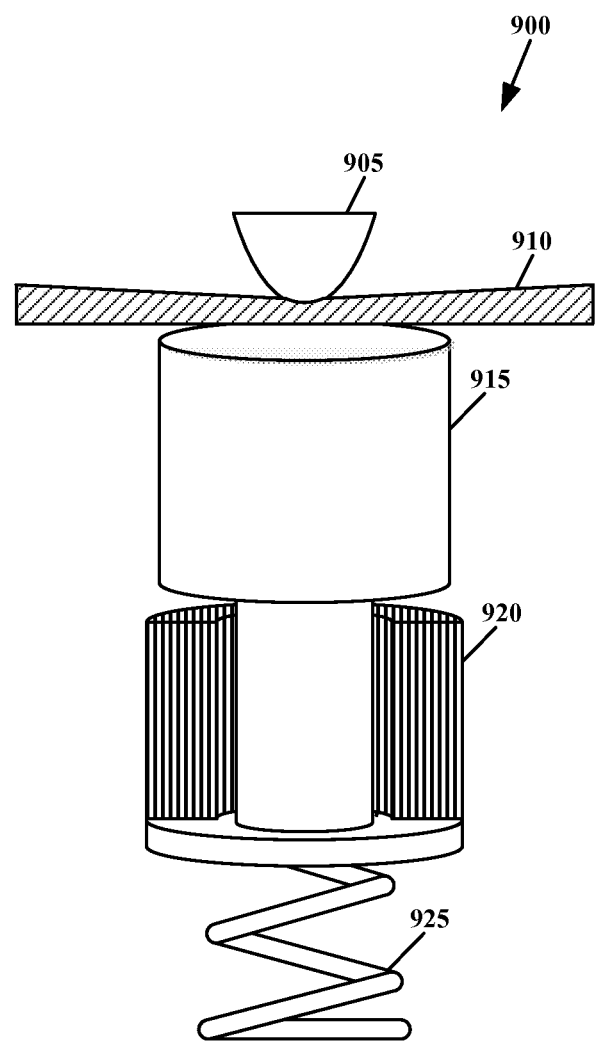
FIG. 9 depicts a cross-section of an illustrative fluid delivery channel flow control system.

Referring to FIG. 9, a cross-section of an illustrative fluid delivery channel flow control system is depicted. As shown in FIG. 9, the fluid delivery channel flow control system 900 may comprise a force concentration point 905 (e.g., a "pinch") and a platen 915 positioned around a fluid delivery channel 910. In an embodiment, the fluid delivery channel 910 may comprise a flexible and deformable tube, such as a polyvinyl chloride (PVC) tube. The fluid delivery channel 910 may be in fluid communication with a source of a medical fluid (not shown), which may be pumped through the fluid delivery channel using a pump (not shown).

As the fluid is pumped through the fluid delivery channel 910 at one or more flow rates, the flow of fluid through the fluid delivery channel may be controlled by changing the distance between the force concentration point 905 and the platen 915. For example, the distance between the force concentration point 905 and the platen 915 may be reduced, thereby squeezing or pinching the fluid delivery channel 910. Pinching the fluid delivery channel 910 may operate to restrict the flow of a fluid in the fluid delivery channel. The flow may even be stopped by squeezing the fluid delivery channel 910 until the flow is cut off. The flow may be increased by expanding (e.g., removing a force squeezing the fluid delivery channel 910) the distance between the force concentration point 905 and the platen 915, allowing the fluid delivery channel to return to its original shape and allowing fluid flow to resume. As such, the fluid delivery channel flow control system 900 may operate as a "pinch valve" configured to pinch the fluid delivery channel 910 to decrease, or even stop, the flow of a fluid within the fluid delivery channel and to stop or reduce the pinching to increase the flow of the fluid.

The distance between the force concentration point 905 and the platen 915 may be increased or decreased through various processes. According to some embodiments, the fluid delivery channel flow control system 900 may be configured to provide a force that moves the force concentration point 905 toward the platen 915 and/or that moves the platen toward the force concentration point.

In an embodiment, a spring 925 may provide at least part of a force that moves the force concentration point 905 and the platen 915 closer together. In another embodiment, an electromagnet 920 may be energized to overcome the spring force and move the force concentration point 905 and the platen 915 farther apart. Embodiments are not limited to the spring 925 and/or an electromagnet 920 depicted in FIG. 1, as these are for illustrative purposes only. Any device, mechanism, or other element capable of moving the force concentration point 905 and/or the platen 915 closer together and/or farther apart is contemplated herein. For instance, some embodiments may use pneumatic and/or hydraulic cylinders.

According to some embodiments, one or more components of a fluid delivery channel flow control system 900 may be configured to measure one or more properties of fluid traveling through the fluid delivery channel 910. For example, the platen 915 may be configured with a sensor for detecting a property of fluid moving through the fluid delivery channel 910 in the section of the fluid delivery channel adjacent to the platen.

Figure 10A:
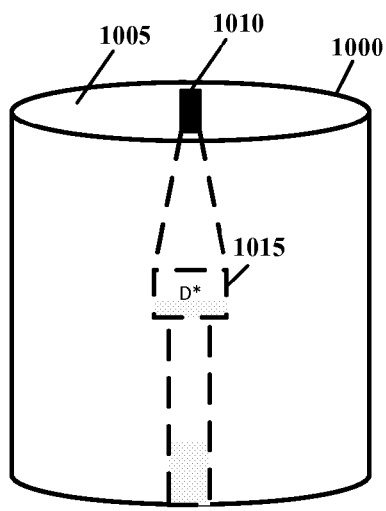
FIGS. 10A and 10B depict different views of an illustrative platen configured to measure a property of a fluid according to an embodiment.
Figure 10B:
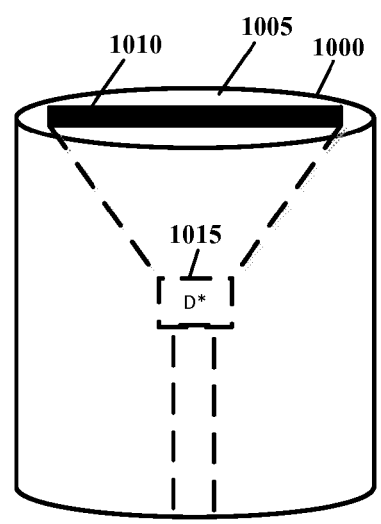

FIGS. 10A and 10B depict different views of an illustrative platen configured to measure a property of a fluid according to an embodiment. As shown in FIGS. 10A and 10B, a platen 1000 may include an aperture 1010 on a face 1005 of a platen that contacts a fluid delivery channel (not shown). FIG. 10A depicts a view of the platen 1000 parallel to a longitudinal axis of the aperture 1010, while FIG. 10B depicts a view of the platen perpendicular to the longitudinal axis of the aperture. The aperture 1010 may be tapered and may provide a narrow opening for a detector 1015 to detect properties of a fluid in a fluid delivery channel. As shown in FIGS. 10A and 10B, the detector 1015 may be located at the focus of the tapered aperture 1010.

Although the aperture 1010 is depicted in FIGS. 10A and 10B as having a substantially rectangular shape, embodiments are not so limited, as this is for illustrative purposes only. The aperture 1010 may be formed of any shape and/or size capable of operating according to embodiments described herein. The aperture 1010 may be hollow or substantially hollow or the aperture may have one or more materials (not shown) disposed therein. In some embodiments, the aperture 1010 may be filled with one or more materials such that the platen 1000 may present a flat and/or smooth or a substantially flat and/or smooth surface for contacting a fluid delivery channel. Such embodiments may operate, among other things, to prolong the life of a fluid delivery channel and to provide a seal against leaks or debris. In these embodiments, the one or more materials may be configured such that a detector 1015 may detect properties of a fluid in a fluid delivery channel through and/or around the one or more materials. In an embodiment, a platen 1000 configured to measure radiation may comprise one or more materials arranged therein and configured to present low attenuation to the radiation being measured. For instance, the aperture may be at least partially filled with a type of plastic if the radiation comprises X-ray or gamma ray photons.

In an embodiment, the platen 1000 may be used to detect the radioactivity of a radioactive fluid in a fluid delivery channel. In such an embodiment, the platen 1000 may include material having adequate radiation shielding properties, for example, to shield the detector 1015 from radioactivity and/or to minimize the sensitivity of the detector to any sources of radiation (or other detected properties), except for radiation emanating from immediately in front of the aperture 1010. For example, the platen 1000 may shield the detector 1015 from radioactivity emanating from other segments of a fluid delivery channel. In a non-limiting example, the platen 1000 may include tungsten, for instance, formed using a wire electrical discharge machining (EDM) process. The detector 1015 may include various suitable detectors, including, without limitation, PIN diodes, semiconductor devices, and miniature Geiger-Mueller tubes.

The platen 1000 is not limited to measuring radioactivity and related properties, as the platen may be configured to measure any fluid property capable of being detected according to embodiments described herein. Non-limiting examples of fluid properties that may be measured using the platen 1000 include temperature, optical properties, presence/absence of fluid, and/or flow rate.

Figure 11:
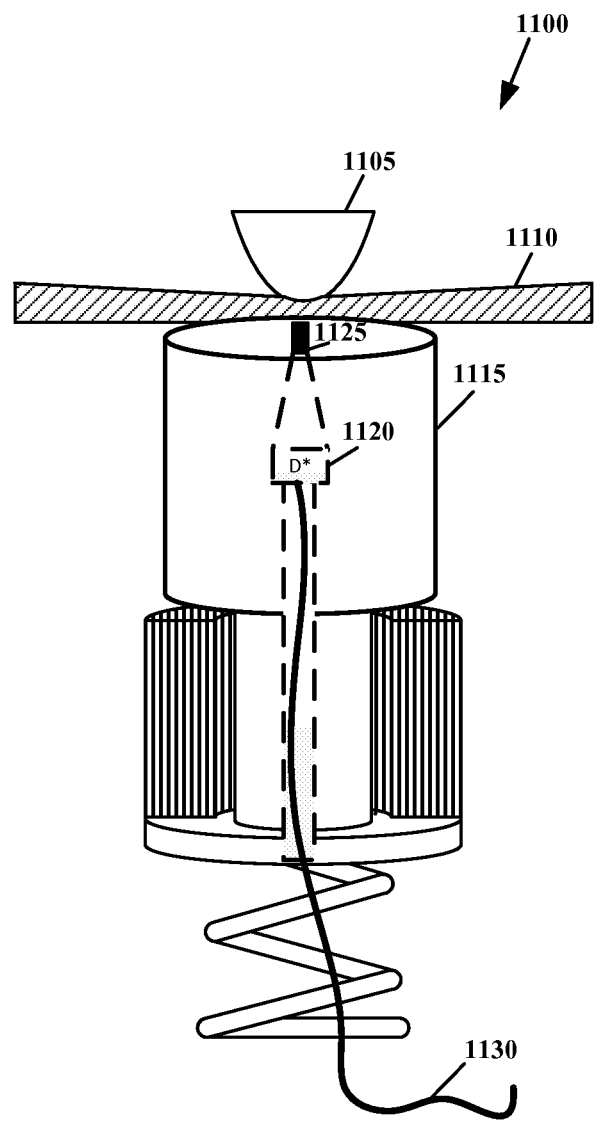
FIG. 11 depicts an illustrative fluid delivery channel flow control system comprising a platen configured to measure properties of a fluid.

FIG. 11 depicts an illustrative fluid delivery channel flow control and liquid property measurement system comprising a platen configured to measure properties of a fluid. As shown in FIG. 11, the fluid delivery channel flow control system 1100 may comprise a force concentration element 1105, such as a backing or capture plate, and a platen 1115 positioned around a fluid delivery channel 1110. In an embodiment, the force concentration element 1105 may be shaped such that it serves as a force concentration point to affect or control flow through the fluid delivery channel 1110. In an embodiment, the force concentration element 1105 may have a substantially broad shape and may be configured to consistently and repeatedly orientate the fluid channel 1105 with respect to the aperture 1125.

In an embodiment, the force concentration element 1105 may include a dense material such as tungsten. In another embodiment, the dense material may be sufficiently thick such that it reduces the amount of or eliminates energy from outside the fluid channel 1105 from impinging on the detector 1120. The platen 1115 may include an aperture 1125 and a detector 1120 arranged within the aperture and configured to detect one or more properties of a fluid in the fluid delivery channel 1110. In an embodiment, the detector 1120 may be in operable communication with a cable 1130, wire, or other element configured to connect the detector to a power source and/or detection electronics. In another embodiment, the power source, detection electronics, and/or portions thereof may be incorporated into the detector 1125 and/or the platen 1115.

According to some embodiments, the force concentration element 1105 may include a channel, ridges, and/or other physical structures (not shown) to hold fluid delivery channel 1110. By holding the fluid delivery channel 1110 in a consistent position, the geometry may be known and the system can determine a fluid property from the detector 1120 measurement and the known geometry.

In an embodiment, a motor may be used to move the force concentration element 1105, for example, in a direction parallel to or over the surface of the platen 1115 (into and out of the plane of FIG. 11), such that the fluid delivery channel 1110 may change position with respect to the aperture 1125. In this embodiment, a computing device (for example, computing device 800 of FIG. 8) may use information about the geometry and position of the fluid delivery channel 1110 and supporting elements to determine the desired fluid property. For example, if the property to be measured is the amount or concentration of radioactivity in the fluid channel 1110, moving the force concentration element 1105 from one side of the aperture to the other may provide information about the position of the center of the fluid channel 1110, maximum readout, fluid channel width, or the like, allowing the computing device to determine concentration while accounting for variety and imperfections in other aspects of the system. Thus, in some of the embodiments described with respect to FIG. 11, the system may accurately measure a property of the fluid using both the output of a sensor 1120 and position or other system configuration information that may change during normal operation of the system.

Without further analysis, the foregoing will so fully reveal the substance of these embodiments that others can, by applying current knowledge, readily adapt it for various applications without omitting features that, from the standpoint of prior art, fairly constitute characteristics of the generic or specific aspects of the embodiments disclosed herein.

If not otherwise stated herein, it may be assumed that all components and/or processes described heretofore may, if appropriate, be considered to be interchangeable with similar components and/or processes disclosed elsewhere in the specification, unless an express indication is made to the contrary.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which are also intended to be encompassed by the disclosed embodiments.

What is claimed is:

1. A syringe system comprising:
    a syringe body comprising a proximal open end and at least one distal discharge outlet, the syringe body for housing a liquid substance to be discharged via the at least one discharge outlet;
    a syringe shield covering at least a portion of the syringe body;
    a plunger positioned in the syringe body and forming a seal with an inner wall of the syringe body;
    an automatic injection system comprising an injector piston configured to be received by the proximal open end and to engage the plunger to cause the plunger to move within the syringe body;
    at least one position sensor measuring at least a position of at least one of the plunger and the injector piston in the syringe body;
    at least one radiation sensor positioned within the injector piston and measuring radioactivity of the liquid substance within the syringe body; and
    a computing device in communication with or part of the automatic injection system and in communication with the at least one position sensor to receive position information about at least the position of at least one of the plunger and the injector piston in the syringe body and with the at least one radiation sensor to receive measurements from the at least one radiation sensor measuring the radioactivity of the liquid substance to determine, using the computing device, an injection volume of the liquid substance based on the position information received from the at least one position sensor and the radioactivity of the liquid substance received from the at least one radiation sensor.

2. The syringe system of claim 1, wherein the at least one radiation sensor does not contact the liquid substance when the syringe body houses the liquid substance.

3. The syringe system of claim 1, wherein at least one of the position sensor and the radiation sensor is selected from the group consisting of silicon diodes, scintillators, photomultipliers, semiconductors, solid state crystals, ion chambers, and combinations thereof.

4. The syringe system of claim 1, wherein the liquid substance is a radioactive contrast agent.

5. The syringe system of claim 1, wherein the radioactivity of the liquid substance is spatially dependent on a distance from the at least one radiation sensor.

6. The syringe system of claim 1, wherein at least one of the position sensor and the radiation sensor comprises a plurality of redundant sensors.

7. The syringe system of claim 1, wherein the liquid substance is a radiopharmaceutical selected from $^{64}$Cu diacetyl-bis(N4-methylthiosemicarbazone), $^{18}$F-fluorodeoxyglucose, $^{18}$F-fluoride, 3'-deoxy-3'-[$^{18}$F]fluorothymidine, $^{18}$F-fluoromisonidazole, thallium, gallium, technetium-99m, indium-113m, and strontium-87m.

8. A syringe system comprising:
    a syringe body comprising a proximal open end and at least one distal discharge outlet, the syringe body for housing a liquid substance to be discharged via the at least one discharge outlet;
    a syringe shield covering at least a portion of the syringe body;
    a plunger positioned in the syringe body and forming a seal with an inner wall of the syringe body;
    an injector piston configured to be received in the proximal open end and to engage the plunger to cause the plunger to move within the syringe body;
    at least one position sensor measuring at least a position of at least one of the plunger and the injector piston in the syringe body;
    at least one radiation sensor positioned within the injector piston and measuring radioactivity of the liquid substance within the syringe body; and
    a computing device receiving information from the at least one position sensor about at least the position of at least one of the plunger and the injector piston in the syringe body and receiving measurements from the at least one radiation sensor measuring the radioactivity of the liquid substance to determine, using the computing device, an injection volume of the liquid substance based on the position information received from the at least one position sensor and the radioactivity of the liquid substance received from the at least one radiation sensor.

9. The syringe system of claim 8, wherein at least one of the position sensor and the radiation sensor is selected from the group consisting of silicon diodes, scintillators, photomultipliers, semiconductors, solid state crystals, ion chambers, and combinations thereof.

10. The syringe system of claim 8, wherein the liquid substance is a radioactive contrast agent.

11. The syringe system of claim 8, wherein the radioactivity of the liquid substance is spatially dependent on a distance from the at least one radiation sensor.

12. The syringe system of claim 11, wherein the at least one radiation sensor does not contact the liquid substance when the syringe body houses the liquid substance.

13. The syringe system of claim 8, wherein at least one of the position sensor and the radiation sensor comprises a plurality of redundant sensors.

14. The syringe system of claim 8, wherein the liquid substance is a radiopharmaceutical selected from $^{64}$Cu diacetyl-bis(N4-methylthiosemicarbazone), $^{18}$F-fluorodeoxyglucose, $^{18}$F-fluoride, 3'-deoxy-3'-[$^{18}$F]fluorothymidine, $^{18}$F-fluoromisonidazole, thallium, gallium, technetium-99m, indium-113m, and strontium-87m.

\* \* \* \* \*

UNITED STATES PATENT AND TRADEMARK OFFICE
CERTIFICATE OF CORRECTION

PATENT NO. : 9,623,191 B2  Page 1 of 1
APPLICATION NO. : 13/783226
DATED : April 18, 2017
INVENTOR(S) : Uber et al.

It is certified that error appears in the above-identified patent and that said Letters Patent is hereby corrected as shown below:

In the Specification
In Column 11, Lines 57-58, delete "sensor 730" and insert -- sensor 735 --, therefor.
In Column 20, Lines 51-52, delete "fluid channel 1105" and insert -- fluid channel 1110 --, therefor.
In Column 20, Line 57, delete "fluid channel 1105" and insert -- fluid channel 1110 --, therefor.

Signed and Sealed this
Twenty-sixth Day of September, 2017

Joseph Matal
*Performing the Functions and Duties of the
Under Secretary of Commerce for Intellectual Property and
Director of the United States Patent and Trademark Office*